United States Patent
Sturtevant

(10) Patent No.: US 8,623,046 B2
(45) Date of Patent: Jan. 7, 2014

(54) TREATMENT FOR PATIENTS AFTER REMOVAL OF SAPHENOUS VASCULAR MATERIAL

(75) Inventor: Donald Lee Sturtevant, Prior Lake, MN (US)

(73) Assignees: Donald Lee Sturtevant, Prior Lake, MN (US); James Franklin Drake, Minneapolis, MN (US)

( * ) Notice: Subject to any disclaimer, the term of this patent is extended or adjusted under 35 U.S.C. 154(b) by 1821 days.

(21) Appl. No.: 11/891,421

(22) Filed: Aug. 10, 2007

(65) Prior Publication Data

US 2009/0043277 A1    Feb. 12, 2009

(51) Int. Cl.
*A61M 31/00* (2006.01)
*A61B 17/08* (2006.01)

(52) U.S. Cl.
USPC ..... 606/213; 604/58; 604/93.01; 604/164.13; 604/264

(58) Field of Classification Search
USPC ............ 606/213, 159; 604/164.13, 266, 502, 604/57, 507, 60, 11, 15, 58, 93.01
See application file for complete search history.

(56) References Cited

U.S. PATENT DOCUMENTS

| | | | | |
|---|---|---|---|---|
| 5,061,274 A * | 10/1991 | Kensey | | 606/213 |
| 5,419,765 A * | 5/1995 | Weldon et al. | | 604/99.02 |
| 5,569,291 A | 10/1996 | Pirvitera et al. | | 606/185 |
| 5,649,959 A * | 7/1997 | Hannam et al. | | 606/213 |
| 5,695,514 A | 12/1997 | Chin | | 606/190 |
| 5,913,866 A | 6/1999 | Ginn et al. | | 606/174 |
| 6,004,335 A | 12/1999 | Vaitekunas et al. | | 606/169 |
| 6,007,551 A | 12/1999 | Peifer et al. | | 606/140 |
| 6,019,771 A | 2/2000 | Bennett et al. | | 606/159 |
| 6,022,313 A | 2/2000 | Ginn et al. | | 600/114 |
| 6,074,402 A | 6/2000 | Peifer et al. | | 606/139 |
| 6,099,535 A | 8/2000 | Lamport et al. | | 606/140 |
| 6,143,005 A | 11/2000 | Yoon et al. | | 606/148 |
| 6,149,659 A | 11/2000 | Ahmed | | 606/140 |
| 6,193,653 B1 | 2/2001 | Evans et al. | | 600/210 |
| 6,206,823 B1 | 3/2001 | Kolata et al. | | 600/129 |
| 6,214,028 B1 | 4/2001 | Yoon et al. | | 606/205 |
| 6,241,740 B1 | 6/2001 | Davis et al. | | 606/139 |
| 6,352,544 B1 | 3/2002 | Spitz | | 606/159 |
| 6,375,635 B1 | 4/2002 | Moutafis et al. | | 604/43 |
| 6,464,685 B1 | 10/2002 | Suzuki et al. | | 604/534 |
| 6,464,708 B1 | 10/2002 | Higuma et al. | | 606/140 |
| 6,475,177 B1 | 11/2002 | Suzuki | | 604/11 |
| 6,520,975 B2 * | 2/2003 | Branco | | 606/159 |
| 6,527,786 B1 | 3/2003 | Davis et al. | | 606/151 |
| 6,565,578 B1 | 5/2003 | Peifer et al. | | 606/139 |
| 6,607,542 B1 | 8/2003 | Wild | | 606/157 |
| 6,610,026 B2 * | 8/2003 | Cragg et al. | | 604/15 |
| 6,610,072 B1 | 8/2003 | Christy et al. | | 606/148 |
| 6,632,228 B2 | 10/2003 | Fortier et al. | | 606/140 |
| 6,656,176 B2 | 12/2003 | Hess et al. | | 606/51 |

(Continued)

*Primary Examiner* — Corrine M McDermott
*Assistant Examiner* — Christopher L Templeton
(74) *Attorney, Agent, or Firm* — Mark A. Litman & Associates, P.A.

(57) ABSTRACT

A device and method for using the device is used for clotting volumes created postoperatively. The device is inserted into a cavity formed by removal of tissue or organ within a patient. The device may have a flexible tubing having a surface material; a blood clotting material enclosed within the surface material of the tubing; a guidewire associated with the device that when placed under tension, stabilizes the tubing radially or longitudinally; and the surface material of the tubing being removable from the enclosed blood clotting material while the guidewire is under tension.

9 Claims, 2 Drawing Sheets

(56) References Cited

U.S. PATENT DOCUMENTS

| | | | |
|---|---|---|---|
| 6,660,016 B2 | 12/2003 | Lindsay | 606/159 |
| 6,679,892 B2 | 1/2004 | Guido et al. | 606/113 |
| 6,685,713 B1 | 2/2004 | Ahmed | 606/140 |
| 6,730,101 B1 | 5/2004 | Peifer et al. | 606/140 |
| 6,818,003 B2 | 11/2004 | Genovesi | 606/159 |
| 6,964,658 B2 * | 11/2005 | Ashby et al. | 604/523 |
| 2003/0065348 A1 | 4/2003 | Hess et al. | 606/159 |
| 2004/0122458 A1 | 6/2004 | Opie et al. | 606/159 |
| 2004/0204725 A1 | 10/2004 | Bayer | 606/159 |
| 2005/0004586 A1 | 1/2005 | Suval | 606/159 |
| 2005/0070940 A1 | 3/2005 | Genovesi et al. | 606/159 |
| 2005/0096677 A1 | 5/2005 | Weilman et al. | 606/159 |
| 2007/0098753 A1 | 5/2007 | Falotico et al. | 424/423 |
| 2007/0128181 A1 | 6/2007 | Mangano | 424/94.63 |
| 2008/0004657 A1 * | 1/2008 | Obermiller et al. | 606/213 |
| 2008/0161843 A1 * | 7/2008 | Clague et al. | 606/167 |

* cited by examiner

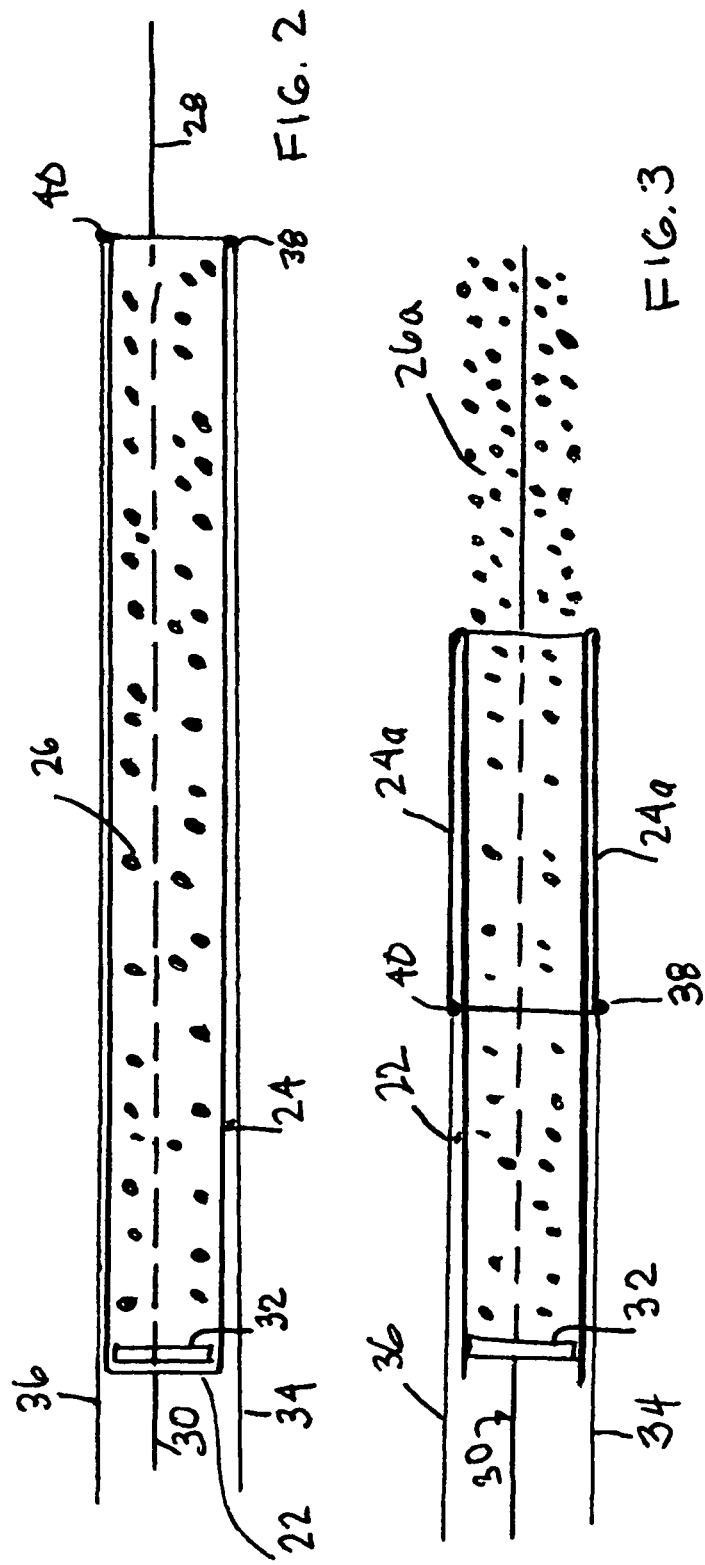

TREATMENT FOR PATIENTS AFTER REMOVAL OF SAPHENOUS VASCULAR MATERIAL

BACKGROUND OF THE INVENTION

1. Field of the Invention

The present invention relates to vascular transplants, to harvesting of vascular material for transplanting and for devices, materials and methods for the treatment of post-operative regions and cavities formed in the harvesting of vascular material to reduce post-operative complications.

2. Background of the Art

Post-surgical complications are a significant source of morbidity and mortality, and healthcare expenditure. For cardiac surgery, approximately one million patients undergo such every year, and approximately one in six develops a serious major organ complication relating to the heart, brain, kidney, GI tract and lung (Mangano, et al., 1997, J. Intensive Care Med. 12:148-160). Yet despite numerous advances in monitoring and technique, no drug has been shown to reduce or prevent these complications. The preoccupation has been with bleeding, and drugs are now used to prevent such. However, drugs which inhibit bleeding generally cause thrombosis, and therefore may induce ischemia and irreversible organ injury (Cosgrove, et al., 1992, Ann. Thorac. Surg. 54: 1031-36).

For noncardiac surgery, approximately 250 million patients undergo such every year, and approximately four percent develop a serious major organ complication relating to the heart. As well, concerns for bleeding predominate, and drugs preventing thrombosis (anti-platelet, anti-clotting) are virtually contraindicated (Eagle, et al, 1999, JACC 34:1262-1347; Pearson, et al, 1994, Circulation 90:3125-33; Baumgartner, et al., 1994, Johns Hopkins Manual of Surgical Care, Mosby Yearbook, St. Louis). However, for both cardiac and noncardiac surgery, marked excitotoxic and inflammatory responses occur for days after surgery, if not months after surgery. Such markedly exaggerated responses are associated with platelet and clotting factor activation, which may precipitate thrombosis.

Although recognized as a possibility, such agents are relatively—and in some cases (fibrinolytics), absolutely—contra-indicated because of fear of excessive hemorrhage at the surgical site, as well as at other sites. Further, some believe—especially after cardiac surgery—that platelet and clotting factor function are depressed after surgery, so that thrombosis is not an issue. Thus, no effort has been made to investigate the use of anti-clotting agents immediately following surgery.

Finally, perioperative events manifest over six to eight months or longer; thus, continuation of use of such anti-clotting agents throughout the in-hospital, and then post-discharge course, is rational.

Many individuals suffer from circulatory disease caused by a progressive blockage of the blood vessels that perfuse the heart and other major organs. More severe blockage of blood vessels in such individuals often leads to hypertension, ischemic injury, stroke, or myocardial infarction. Atherosclerotic lesions, which limit or obstruct coronary blood flow, are the major cause of ischemic heart disease. Percutaneous transluminal coronary angioplasty is a medical procedure whose purpose is to increase blood flow through an artery. Percutaneous transluminal coronary angioplasty is the predominant treatment for coronary vessel stenosis. The increasing use of this procedure is attributable to its relatively high success rate and its minimal invasiveness compared with coronary bypass surgery. A limitation associated with percutaneous transluminal coronary angioplasty is the abrupt closure of the vessel, which may occur immediately after the procedure and restenosis, which occurs gradually following the procedure. Additionally, restenosis is a chronic problem in patients who have undergone saphenous vein bypass grafting. The mechanism of acute occlusion appears to involve several factors and may result from vascular recoil with resultant closure of the artery and/or deposition of blood platelets and fibrin along the damaged length of the newly opened blood vessel.

Restenosis after percutaneous transluminal coronary angioplasty is a more gradual process initiated by vascular injury. Multiple processes, including thrombosis, inflammation, growth factor and cytokine release, cell proliferation, cell migration and extracellular matrix synthesis each contribute to the restenotic process.

While the exact mechanism of restenosis is not completely understood, the general aspects of the restenosis process have been identified. In the normal arterial wall, smooth muscle cells proliferate at a low rate, approximately less than 0.1 percent per day. Smooth muscle cells in the vessel walls exist in a contractile phenotype characterized by eighty to ninety percent of the cell cytoplasmic volume occupied with the contractile apparatus. Endoplasmic reticulum, Golgi, and free ribosomes are few and are located in the perinuclear region. Extracellular matrix surrounds the smooth muscle cells and is rich in heparin-like glycosylaminoglycans, which are believed to be responsible for maintaining smooth muscle cells in the contractile phenotypic state.

Published US Patent Application 20070098753 (Falotico) describes the use of coating agents on implements to prevent post-surgery effects causing inflammation and clotting.

Published US Patent Application 2007/0128181 provides methods of preventing or reducing post-surgical morbidity and mortality. Significantly, the prevention or reduction of post-surgical morbidity and mortality can extend beyond hospitalization. In certain aspects, the methods comprise the perioperative and long-term administration of a blood clotting inhibitor to prevent or reduce post-surgical complications. The blood clotting inhibitor can be administered perioperatively, that is, prior to, during and/or after surgery and after hospital discharge, for example, six months, one year or longer.

Healthy blood vessels are typically harvested to repair damaged vessels in other more critical parts of a human circulatory system. In particular, the saphenous vein is harvested from a patient's leg and utilized in bypass surgery where damaged and blocked arteries of the heart region of the patient are bypassed with the healthy blood vessel harvested.

Typically, the surgeon will harvest an appropriate length of the leg vessel requiring that the vessel be safely separated from side branch vessels and leg tissue, followed by an appropriate dissection of the end of the harvested vessel. In early surgery of this type, incisions were made along the length of the saphenous vessel to be harvested which was then dissected from the surrounding tissue. More modern surgical techniques have been developed and are utilizing a broad variety of vessel harvesting instruments and apparatus which greatly reduce the trauma to the patient. The following U.S. patents appear to represent at least a substantial portion of this more modern vessel harvesting technology.

Conventional deployment systems used to place medicaments in wound channels are described in Suzuki U.S. Pat. No. 6,475,177. These systems rely on syringe-like configurations in which the piston is held in place by a rigid rod. This design results in a rigid, inflexible device since the rod-piston assembly must support the compressive forces generated as the outer tube is deployed.

U.S. Pat. No. 6,660,016 to Lindsay discloses an endoscopic apparatus for harvesting blood vessels including an endoscopic barrel with a plurality of lumens, a handle disposed at a proximal end of the barrel and at lest one member for dissecting and cauterizing a blood vessel. An invention related to devices and methods for removing veins is taught by Spitz in U.S. Pat. No. 6,352,544.

David, et al., in U.S. Pat. No. 6,241,740 teaches a system and medical device for endoscopically ligating and cutting a body vessel, the improvements including a hinged jaw, an improved delivery system of a ligating clip and a rotating cutting instrument. A surgical instrument comprising an elongated hollow shaft having a longitudinal axis, a lumen, and an optical penetrating tip having a cylindrical portion attached to the distal end of the hollow shaft is taught by Kolata, et al. in U.S. Pat. No. 6,206,823.

U.S. Pat. No. 6,193,653 to Evans, et al. discloses methods and devices for harvesting vessels comprising a shaft having a handle mounted on one end and a dissecting tip on the other end. A light source is further optionally included and methods for transilluminating a vessel, dissecting the vessel, transecting the vessel and removing the vessel from the body are disclosed.

A method and apparatus for the minimally invasive harvesting of veins is taught by Ginn, et al. in U.S. Pat. No. 6,022,313 and devices and methods for minimally invasive harvesting of a vessel are shown in U.S. Pat. No. 5,913,866. U.S. Pat. No. 6,019,771 to Bennett, et al. teaches similar devices and methods as Ginn, et al. and we note that these three patents have been assigned to Cardiothoracic Systems, Inc.

U.S. Published Application US2005/0070940 to Genovesi, et al. teaches a method and device for harvesting vessels comprising a cannula-like device including means for identification, capture, manipulation, hemostasis and cleavage of branch vessels. That published application is a continuation application of U.S. Pat. No. 6,818,003 directed to a method and device for harvesting vessels. The harvesting cannula is configured as an elongated, hollow tube and comprised of three sections: a harvesting head, a tubular control segment and a sliding operation arm.

Another published application to Hess, et al., US 2003/0065348 and U.S. Pat. No. 6,656,176, disclose endoscopic vessel harvesting devices and methods. The method comprises locating the vessel, inserting the device through an incision, dissecting the vessel from the surrounding tissue and capturing vessels. The device comprises a headpiece having electrodes for ligation, a shaft having a lumen, and a vessel capturing means.

Other published applications and issued patents are known to applicant as follows: U.S. Pat. No. 6,527,786 to Davis, et al.; U.S. Pat. No. 6,679,892 to Guido, et al.; U.S. Pat. No. 6,464,708 to Higuma, et al.; U.S. Pat. No. 6,464,685 to Suzuki, et al.; U.S. Pat. No. 5,695,514 to Chin; U.S. Pat. No. 5,569,291 to Pirvitera, et al.; U.S. Pat. No. 6,004,335 to Vaitekunas, et al.; U.S. Pat. No. 6,375,635 to Moutafis, et al.; U.S. Pat. No. 6,214,028 to Yoon, et al.; U.S. Pat. No. 6,149,659 to Ahmed; U.S. Pat. No. 6,143,005 to Yoon, et al.; U.S. Pat. No. 6,099,535 to Lamport, et al.; U.S. Pat. No. 6,074,402 to Peifer, et al.; U.S. Pat. No. 6,007,551 to Peifer, et al.; U.S. Pat. No. 6,730,101 to Peifer, et al.; U.S. Pat. No. 6,565,578 to Peifer, et al.; U.S. Pat. No. 6,685,713 to Ahmed; U.S. Pat. No. 6,610,072 to Christy, et al.; U.S. Pat. No. 6,632,228 to Fortier, et al.; U.S. Pat. No. 6,607,542 to Wild; U.S. Publ. US2004/0122458 to Opie, et al.; U.S. Publ. US2005/0004586 to Suval; U.S. Publ. US2004/0204725 to Bayer; and U.S. Publ. US2005/0096677 to Wellman, et al.

As can be seen from a review of this technology, the implications of post-operative stress and collateral damage to tissue and residual effects from the surgery can have serious effects. The present technology attempts to reduce the post-operative effects from vascular harvesting such as veinous or arterial harvesting for transplantation, especially intrapatient transplant of vascular material.

SUMMARY OF THE INVENTION

Methods and devices are describes for the insertion of flexible tubing into surgical cavities left by vein harvesting and the release of volumes of clotting agent in a manner that enables filling of the cavity with a blood clot to prevent the retention of an open volume within a patient. A flexible catheter-like element is inserted into the volume, and clotting agent is released into the volume. The flexible device may be stiffened during delivery to stabilize its position within the cavity and a covering for the clotting agent removed. All references cited herein are incorporated herein in their entirety. By contrast to the prior art, the present device relies on tensile forces in the wire/cord to resist the forces generated during deployment. This feature allows the entire device to be flexible for easy insertion into curved or complex wound geometries that would not accommodate the rigid devices of previous art.

BRIEF DESCRIPTION OF THE FIGURES

FIG. 2 shows stiffening of a guidewire to stabilize the device of FIG. 1 prior to delivery of carried clotting agent. Retraction wires are also shown.

FIG. 3 shows partial removal of a covering of the device of claim 1 and release of clotting agent into the cavity formed by vein harvesting. Tension on retraction wires is shown to withdraw the cover on the enclosed clotting agent.

DETAILED DESCRIPTION OF THE INVENTION

Figure 1:
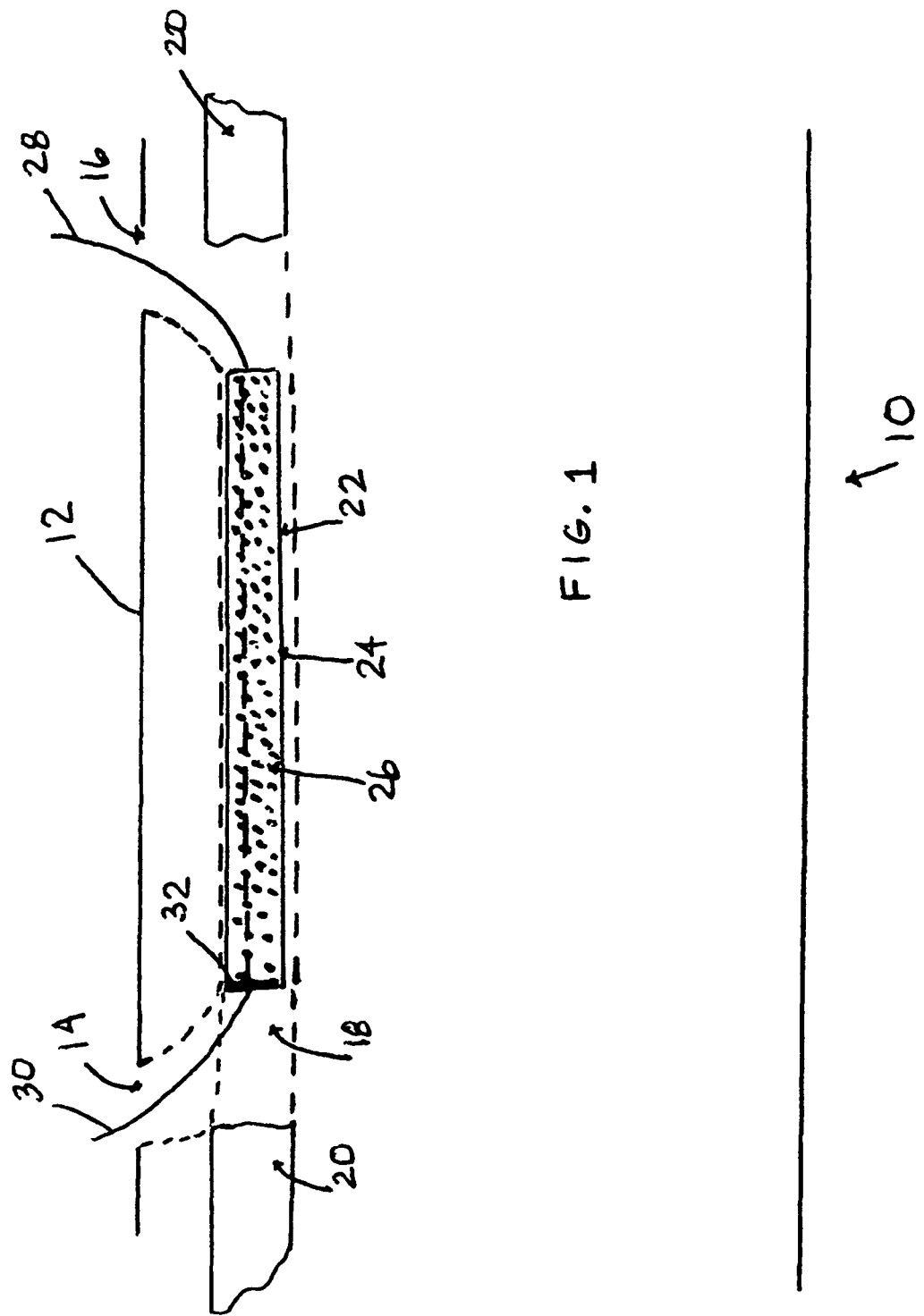
FIG. 1 shows a device according to the present technology inserted within a cavity formed from vein harvesting.

After harvesting of vascular material, the removal of the saphenous vein or other vascular material leaves a cavity or tunnel in the region where the vascular material previously resided. In addition to the removed volume of saphenous material, there are numerous smaller blood vessels that have been cut or ripped from the removed saphenous vessel during harvesting. These vessels may bleed into the remaining cavity and be a source of continued pain, inflammation and other post-operative trauma and complications to the site. Attempts to provide to treat the area have been of limited success. These attempts to provide treatment have usually involved the use of syringes or rigid catheters to provide material to the sight. Applicant's previous and undisclosed attempts to deliver clotting agent by direct injection of clotting agent have resulted in excessive localized clotting without substantive filling of the cavity. For example, by injecting (with a syringe or other rigid element) clotting agent into a region, a rapid clotting agent will form localized clots and tend to clog the outlet (from blood backfeed into the syringe opening), preventing smooth delivery. A slow acting clotting agent will tends to disperse and be carried to unwanted regions and be ineffective in filling the cavity. Neither of these results are satisfactory and can actually have adverse effects by the random formation of clots within the patient or the forming of small clots that may migrate.

The present technology addresses the issues and problems surrounding harvesting of vessel, especially for use in transplantation of vessels within a patient by both methods and devices that can deliver clotting agents in a controlled, directed and effective manner to fill cavities or tunnels or voids left by removal of saphenous vessels during harvesting.

The technology of the present disclosure comprises both methods and devices. A device for insertion into a cavity formed by removal of tissue or organ within a patient, or by deformation or damage to tissues (e.g., as by insertion of a device, including a needle, crocar, angioplasty device, surgical tool, and the like) may comprise a flexible tubing having a surface material; a blood clotting material is enclosed within the surface material of the tubing; a guidewire associated with the device that when placed under tension, stabilizes the tubing radially; and the surface material of the tubing is removable from the enclosed blood clotting material while the guidewire is under tension. The surface material may be sufficiently thin and flexible so as to be slideably retractable over itself to leave a volume of blood clotting material behind a volume previously enclosed by retract surface material or may be dispersible or soluble in blood, as with a mannitol or other sugar or biocompatible biodigestible or bioabsorble material. The blood clotting material is preferably a solid particulate material enclosed within the surface material, but may alternatively be a liquid composition enclosed within the surface material. The liquid would have to be initially prevented from leaking out of both ends, while the solid particulate tends to be more stable within the tube. A barrier element should be provided on an end of the device and within the device that prevents particulate material from being forced out of an end of the device towards which the surface material is retracted. The device may have attachment positions (hooks, holes and the like) that are provided for withdrawal elements that can retract the surface material. The withdrawal elements may comprise filamentary materials selected from the group consisting of metal, polymer, ceramic, glass, graphite and combinations thereof. The flexible device may be required to have the flexible tubing, when filled with blood clotting agent, capable of being wrapped around an 8 cm or a 4 cm mandrel without cracking of the surface material. The powder should not be so tightly packed or bound (e.g., with rigid binder that will not easily break) as to prevent the tubing from moving in a serpentine pathway through a cavity, which requires insertion through an opening in the patient and then adjustment in direction along the pathway of the cavity, which requires a number of twists and turns.

A method for filling an internal volume within a patient created by a surgical procedure where there is blood available within the volume according to the present invention may include the steps such as: inserting a flexible tubing having a surface material and a blood clotting material enclosed within the surface material of the tubing into the volume; and removing the surface material to leave a volume of blood clotting material within the volume. Tension should be applied to the device, as by guidewires in advance of removing the surface material. The surface material is preferably retracted from one end of the device to another end of the device to remove the surface material and leave the volume of blood clotting material. A barrier may be present within the device to prevent exiting of blood clotting material from the device in a direction towards which the surface material is being retracted. The volume usually has been created by harvesting of vessels from a patient.

A review of the figures will assist in a further understanding of the present technology. FIG. 1 shows a limb 10 of a patient with covering skin 12 and both an entrance 16 and exit 14 to a cavity 18 within the limb 10. Guidewires 28 and 30 are shown at both ends of the device 22. The device 22 has a surface material 24 that encloses the blood clotting material 26, here shown as a free flowing particulate material, such as Sephadex™ powder. Truncated vessel ends 20 are shown, from which vascular material had been harvested previously.

FIG. 2 shows the straightened (by tension) guidewires 30 and 28. The tension also acts to stabilize the device 22 and its surface 24 by translated tension through the length of the device 22 and through the particulate 26 within the device 22. The barrier 32 at one end of the device 22 (the end towards which the surface material 24 will be retracted) prevents the particulates 26 (or other enclosed materials) from being pulled backwards out of the end of the device 22 towards guidewire 30. Also shown in the FIG. 2 are two connecting elements 38 and 40 at a distal end of the device 22 to which are attached wires 34 and 36.

FIG. 3 shows the device 22 with the withdrawing wires 36 and 34 pulled back, drawing and retracting surface material 24a over the surface material 24. A cut may be provided within the surface material to assist retraction of the surface material 24. Also shown is the use of connector beads as the attachment elements 38 and 40 provide a slide surface against the outer surface material 24 to facilitate retraction as the wires 36 and 34 are pulled. A volume of particulate blood clotting agent 26a is shown left behind the retracted surface material 24a. If this is a fast clotting material, blood will rapidly (a few seconds) clot the volume in place, forming a solid clot filling the void created by removal of the saphenous tissue. After substantial or full retraction of the surface material 24a, the guidewire 30 may be used to remove the barrier 32 from the patient.

The flexible tubing used as the surface material may be a synthetic elastomer, synthetic polymer, may be a braided fabric material, continuous film and the like. Silicone polymers, silicone elastomers, polyamides, polyurethanes, polystyrene-butadiene copolymers and terpolymers (e.g., with acrylonitrile and the like), polyvinyl resins, polyacrylates and natural materials that are bioacceptable for short terms may be used. Even braided thin fabric metal or ceramic fibers may be used.

Preferred rapid-acting clotting agents are compositions which may be used for the enhancement of the clotting of blood in animals, including mammals, avians and reptiles comprises porous particulate material which is applied to the wound when there is blood in a liquid or only partially clotted state (e.g., where it may wet the particles). The particles may be applied to the wound area either as a free flowing powder of the particles, as an association of particles in or on a carrier and may optionally contain conventional clotting agents with the particles. The particle application should enable direct contact of the particles with the flow of blood, preferably without any non-clotting intermediate film or material between the blood at the site of the wound and the clotting particles.

The particles may generally have a size of from about 1 to 1000 micrometers, or 1 to 500 micrometers, but the size may be varied by one ordinarily skilled in the art to suit a particular use or type of patient and depending on the ability of a carrier to support the particles with their optional selection of sizes. Examples of specific materials useful in the practice of the present invention comprise porous materials from within the classes of polysaccharides, cellulosics, polymers (natural and synthetic), inorganic oxides, ceramics, zeolites, glasses, metals, and composites. Preferred materials are of course nontoxic and are provided as a sterile supply. The polysaccharides are preferred because of their ready availability and modest cost. The porous particulate polysaccharides may be provided as starch, cellulose and/or pectins, and even chitin may be used (animal sourced from shrimp, crab and lobster, for example). Glycosaccharides or glycoconjugates which are described as associations of the saccharides with either proteins (forming glycoproteins, especially glycolectins) or with a lipid (glycolipid) are also useful. These glycoconjugates appear as oligomeric glycoproteins in cellular membranes. In any event, all of the useful materials must be porous enough to allow blood liquid and low molecular weight blood components to be adsorbed onto the surface and/or absorbed into the surface of the particles. Porosity through the entire particle is often more easily achieved rather than merely etching the surface or roughening the surface of the particles.

Ceramic materials may be provided from the sintering, or sol-gel condensation or dehydration of colloidal dispersions of inorganic oxides such as silica, titanium dioxide, zirconium oxide, zinc oxide, tin oxide, iron oxide, cesium oxide, aluminum oxide and oxides of other metal, alkaline earth, transition, or semimetallic chemical elements, and mixtures thereof. By selection of the initial dispersion size or sol size of the inorganic oxide particles, the rate of dehydration, the temperature at which the dehydration occurs, the shear rate within the composition, and the duration of the dehydration, the porosity of the particles and their size can be readily controlled according the skill of the ordinary artisan.

With regard to cellulosic particles, the natural celluloses or synthetic celluloses (including cellulose acetate, cellulose butyrate, cellulose propionate, etc.) may be exploded or expanded according to techniques described in U.S. Pat. No. 5,817,381 and other cellulose composition treating methods described therein which can provide porous particles, fibers and microfibers of cellulose based materials. Where the porous materials, whether of cellulose or other compositions, have a size which may be too large for a particular application, the particles may be ground or milled to an appropriate size. This can be done by direct mortar and pestle milling, ball milling, crushing (as long as the forces do not compress out all of the porosity), fluidized bed deaggregation and size reduction, and any other available physical process. Where the size of the raw material should be larger than the particle size provided, the smaller particles may be aggregated or bound together under controlled shear conditions with a binder or adhesive until the average particle size is within the desired range.

Porosity may be added to many materials by known manufacturing techniques, such as 1) codispersion with a differentially soluble material, and subsequent dissolution of the more soluble material, 2) particle formation from an emulsion or dispersion, with the liquid component being evaporated or otherwise removed from the solid particle after formation, 3) sintering of particles so as to leave porosity between the sintered or fused particles, 4) binding particles with a slowly soluble binder and partially removing a controlled amount of the binder, 5) providing particles with a two component, two phase system where one component is more readily removed than another solid component (as by thermal degradation, solubilization, decomposition, chemical reaction such as, chemical oxidation, aerial oxidation, chemical decomposition, etc.), and other known process for generating porosity from different or specific types of compositions and materials. Where only surface porosity is needed in a particular clot promoting format, surface etching or abrasion may be sufficient to provide the desired surface porosity.

A particularly desirable and commercially available material comprises polysaccharide beads, such as dextran beads which are available as Sephadex™ beads from Pharmacia Labs. These are normally used in surgery as an aid to debridement of surfaces to help in the removal of damaged tissue and scar tissue from closed wounds. The application of this type of porous bead (and the other types of porous beads such as those formed from crosslinked starch) to open wounds with blood thereon has been found to promote hemostasis, speeding up the formation of clots, and reducing blood loss and the need for continuous cleaning of the wound area. Bleeding from arteries, veins and small capillaries, soft tissue, organs (e.g., liver, kidney, lungs and spleen) can be effectively managed, reduced and eliminated in most cases by application of the particles or beads according to the present invention.

The beads or particles may be free flowing or be supported on or in a containment system. For example, the particles may be loosely adhered with biocompatible binder that may dissolve or will be absorbed or adsorbed by the porous particles or porous beads) and the patients natural biological processes in the cavity with blood thereon. The particles may also be provided in a form where the porous particles or porous beads may be interspersed with fibers, filaments or other particles in a self-supporting structure, entangled within the fibrous elements of a net, web, mesh, fabric or sheet, or embedded in a sheet or film (with the particles exposed to enable adsorption or absorption of blood in contact with the wound). The terms particles and beads are not intended to denote any substantive difference in size, shape or performance of materials and are not asserted as having any distinct differences within the practice of the present invention, but are merely alternative terms. The use of only one term does not intend that the other term is not equally applicable in the context in which the one term is used. The porous particles and porous beads may also be provided as part of a patch system, with a fibrous network associated with the particles to provide a high level of structural integrity and strength to the applied assembly over the wound, even before clotting has occurred. This would be particularly appropriate where the assembly was being used as a stitch replacement or true wound closure system rather than only promoting clotting.

The porous particles may easily be associated with or carry additional, but optional, clotting or wound treating materials or ingredients. For example, it would be desirable to provide the porous particles with antibiotics, antifungal agents (especially where application may be in a tropical environment), topical pain reducing medication, pharmaceuticals, anti-inflammatants, tissue enzyme inhibitors (e.g., epsilon aminocaproic acid, to reduce tissue enzyme production that would weaken the blood clot), and the like. Existing materials which promote clotting or control bleeding would be particularly, such as thrombin, fibrinogen, aprotinin, fibronectin, and factor XIII. However, one of the advantages of the materials which may be used (excluding those derived from animals) is that they are not made from animal components as are the typical clotting or wound treatment materials noted above. As there is always a potential for animal based materials being a source of infection themselves (e.g., viral infection, spongiform encephalopathy, allergic reactions, etc.), the avoidance of animal based products, which can be easily accomplished in the practice of the present invention, is desirable.

The preferred polysaccharide components for the porous particles and porous beads of the present invention may often be made from cross-linked polysaccharides, such as cross-linked dextran (poly[beta-1,6-anhydroglucose]) or starch (poly{alpha-1,4-anhydroglucose]). Dextran is a high molecular eight, water-soluble polysaccharide. It is not metabolized by humans, is non-toxic, and is well tolerated by tissue in most animals, including most humans. There has even been extensive use of solubilized dextrans as plasma substitutes. Similarly, beads prepared by cross linking starch with epichlorohydrin are useful as hemostatic agents and are well tolerated by tissue. The starch particles are enzymatically degraded by tissue alpha-amylases and rapidly removed from the wound site. The Sephadex™. beads specifically mentioned in the description of particularly useful polysaccharides comprise dextran crosslinked with epichlorihydrin. These beads are available in a variety of bead sizes (e.g., 10 to 100 micrometers, with a range of pore size. It is believed that pore sizes on the order of from 5 to 75% of volume may be commercially available and can be expanded to from 5 to 85% by volume or manufactured with those properties from amongst the type of beads described above. The sizes of the pores may also be controlled to act as molecular sieves, the pore size being from 0.5% or 1 to 15% of the largest diameter of the particles or beads. The Sephaex™ beads are promoted as having controlled pore sizes for molecular weight cutoff of molecules during use as a sieve, e.g., with cutoff molecular being provided at different intervals between about 5,000 Daltons and 200,000 Daltons. For example, there are cutoff values specifically for molecular weight sizes of greater than 75,000 Daltons. This implies a particle size of specifically about 10 to 40 microns. These beads will rapidly absorb water, swelling to several times their original diameter and volume (e.g., from 5 to as much as twenty times their volume). Similar technology can be used to produce cross linked starch beads with properties similar to the Sephadex™ particles. Other soluble polysaccharides such as sodium alginate or chitosan can be used to prepare cross linked beads with controlled porosity and size.

What is claimed:

1. A method for filling an internal volume within a patient created by a surgical procedure where there is blood available within the volume comprising:
   inserting a flexible tubing having a surface material and a free-flowing blood clotting material enclosed within the surface material of the tubing into the volume; and
   removing the surface material to leave a volume of free-flowing blood clotting material within the volume from which the surface material has been removed.

2. The method of claim 1 wherein tension is applied to the flexible tubing through guidewires in advance of removing the surface material.

3. The method of claim 2 wherein the volume has been created by harvesting of vessels from a patient and the free-flowing blood clotting material consists essentially of a free-flowing particulate.

4. The method of claim 2 wherein the surface material is retracted from one end of the flexible tubing to another end of the flexible tubing to remove the surface material and leave the volume of free-flowing blood clotting material as a particulate material.

5. The method of claim 4 wherein the volume has been created by harvesting of vessels from a patient and the free-flowing blood clotting material consists essentially of a free-flowing particulate.

6. The method of claim 4 wherein a barrier within the flexible tubing prevents exiting of free-flowing blood clotting material from the flexible tubing in a direction towards which the surface material is being retracted.

7. The method of claim 6 wherein the volume has been created by harvesting of vessels from a patient.

8. The method of claim 1 wherein the volume has been created by harvesting of vessels from a patient and the free-flowing blood clotting material consists essentially of a free-flowing particulate.

9. A method for filling an internal volume within a patient created by a surgical procedure where there is blood available within the volume comprising:
   inserting a flexible tubing having a surface material and a fill consisting essentially of free-flowing blood clotting material enclosed within the surface material of the tubing into the volume; and
   removing the surface material to leave a volume consisting essentially of free-flowing blood clotting material in the blood within the volume from which the surface material has been removed.

* * * * *